(12) United States Patent
Cooper et al.

(10) Patent No.: US 6,854,859 B2
(45) Date of Patent: *Feb. 15, 2005

(54) PEN SIZE LED INSPECTION LAMP FOR DETECTING FLUORESCENT MATERIAL

(75) Inventors: B. William Cooper, Lloyd Harbor, NY (US); Gustavo Garcia, Lake Grove, NY (US)

(73) Assignee: Spectronics Corporation, Westbury, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/215,629

(22) Filed: Aug. 9, 2002

(65) Prior Publication Data

US 2003/0007345 A1 Jan. 9, 2003

Related U.S. Application Data

(63) Continuation-in-part of application No. 09/899,796, filed on Jul. 5, 2001, now Pat. No. 6,491,408.

(51) Int. Cl.[7] .................................................. F21V 33/00
(52) U.S. Cl. ........................ 362/139; 362/184; 362/198; 362/230; 362/800
(58) Field of Search ................................. 362/184, 186, 362/198, 138, 230, 293, 118, 119, 800, 139; 250/504 H

(56) References Cited

U.S. PATENT DOCUMENTS 1,097,023 A   5/1914   Hirsch
2,467,954 A   4/1949   Becker
2,697,128 A   12/1954  Moore (List continued on next page.)

FOREIGN PATENT DOCUMENTS

| GB | 1048606 | 6/1966 |
|----|---------|--------|
| JP | 405311733 A | 11/1993 |
| JP | 407254301 A | 10/1995 |

OTHER PUBLICATIONS

Science Service Historical Image Collection; Smithsonian National Museum of American History, Flexible Flashlight, CD1964026 E&MP26.010, dated Mar. 5, 1944.

Flashlights with Rarity & Value Guide: Early Flashlight Makers and the First 100 Years of Eveready, Arrowpoint Press; Billy T. Utley, p. 234, 2001.

The SnakeLight—http://wps.prenhall.com/esm_giesecke_8/0_8217.1002953–.00.html—Jan. 28, 2004.

*Primary Examiner*—Stephen Husar
*Assistant Examiner*—Sharon Payne
(74) *Attorney, Agent, or Firm*—Drinker Biddle & Reath LLP

(57) ABSTRACT

A pen-size inspection lamp for detecting fluorescent leak detection materials in hard-to-reach areas. The inspection lamp includes a housing, an extendible handle, at least one LED and a mirror assembly. The mirror assembly includes a mirror, a clip for attaching the mirror to the housing, and an arm extending between the clip and the mirror with a hinge connection for rotating the mirror to different reflection angles with respect to the LED.

23 Claims, 9 Drawing Sheets

U.S. PATENT DOCUMENTS

| | | | |
|---|---|---|---|
| 3,103,723 A | | 9/1963 | Becker |
| 4,329,737 A | | 5/1982 | Triller et al. |
| 4,358,708 A | | 11/1982 | Silva et al. |
| 4,597,033 A | | 6/1986 | Meggs et al. |
| 4,947,291 A | | 8/1990 | McDermott |
| 5,034,615 A | | 7/1991 | Rios et al. |
| 5,381,319 A | | 1/1995 | Shiao |
| 5,420,768 A | * | 5/1995 | Kennedy .................... 362/119 |
| 5,521,803 A | | 5/1996 | Eckert et al. |
| 5,567,115 A | | 10/1996 | Carbone |
| 5,647,623 A | | 7/1997 | Shiao |
| 5,711,665 A | | 1/1998 | Adam et al. |
| 5,742,066 A | | 4/1998 | Cavestri |
| 5,788,364 A | | 8/1998 | Cooper et al. |
| 5,804,822 A | | 9/1998 | Brass et al. |
| 5,816,692 A | | 10/1998 | Cooper et al. |
| 5,847,507 A | | 12/1998 | Butterworth et al. |
| 5,906,426 A | | 5/1999 | Farrington et al. |
| 5,951,142 A | * | 9/1999 | Wang et al. ................. 362/109 |
| 5,975,712 A | | 11/1999 | Shiao |
| 5,997,154 A | | 12/1999 | Cooper et al. |
| 6,007,214 A | | 12/1999 | Shiao |
| 6,033,087 A | | 3/2000 | Shozo et al. |
| 6,068,383 A | | 5/2000 | Robertson et al. |
| D430,321 S | | 8/2000 | Sharrah |
| 6,168,288 B1 | | 1/2001 | St. Claire |
| 6,177,678 B1 | | 1/2001 | Brass et al. |
| 6,200,134 B1 | | 3/2001 | Kovac et al. |
| 6,227,679 B1 | | 5/2001 | Zhang et al. |
| 6,280,050 B1 | | 8/2001 | Bird et al. |
| D452,024 S | | 12/2001 | Sharrah |
| 6,390,641 B1 | * | 5/2002 | Liu ............................ 362/118 |
| 6,402,340 B1 | | 6/2002 | Sharrah et al. |
| 6,468,077 B1 | | 10/2002 | Melikechi et al. |
| 6,491,408 B1 | | 12/2002 | Cooper et al. |
| 6,491,409 B1 | | 12/2002 | Sharrah et al. |
| 6,590,220 B1 | | 7/2003 | Kalley et al. ........... 250/504 H |
| 6,742,910 B2 | | 6/2004 | Chen |
| 2002/0079454 A1 | | 6/2002 | Yamada et al. |
| 2003/0010093 A1 | | 1/2003 | Barjesteh |
| 2003/0095408 A1 | | 5/2003 | Opolka |

* cited by examiner

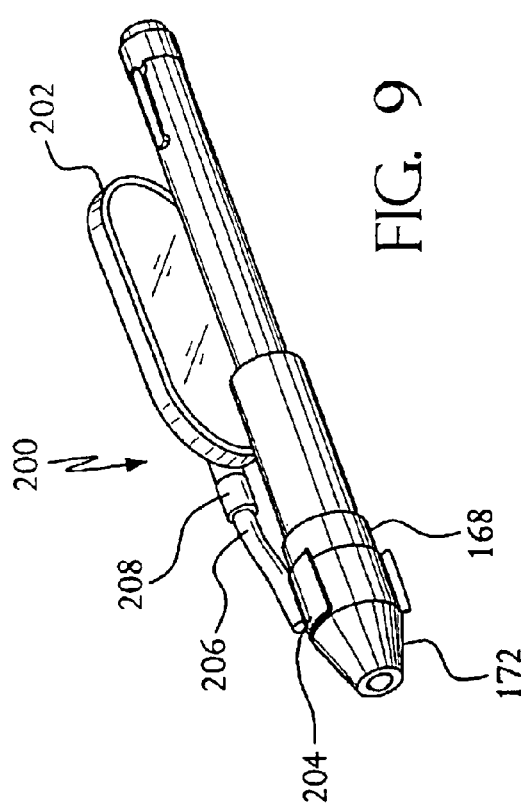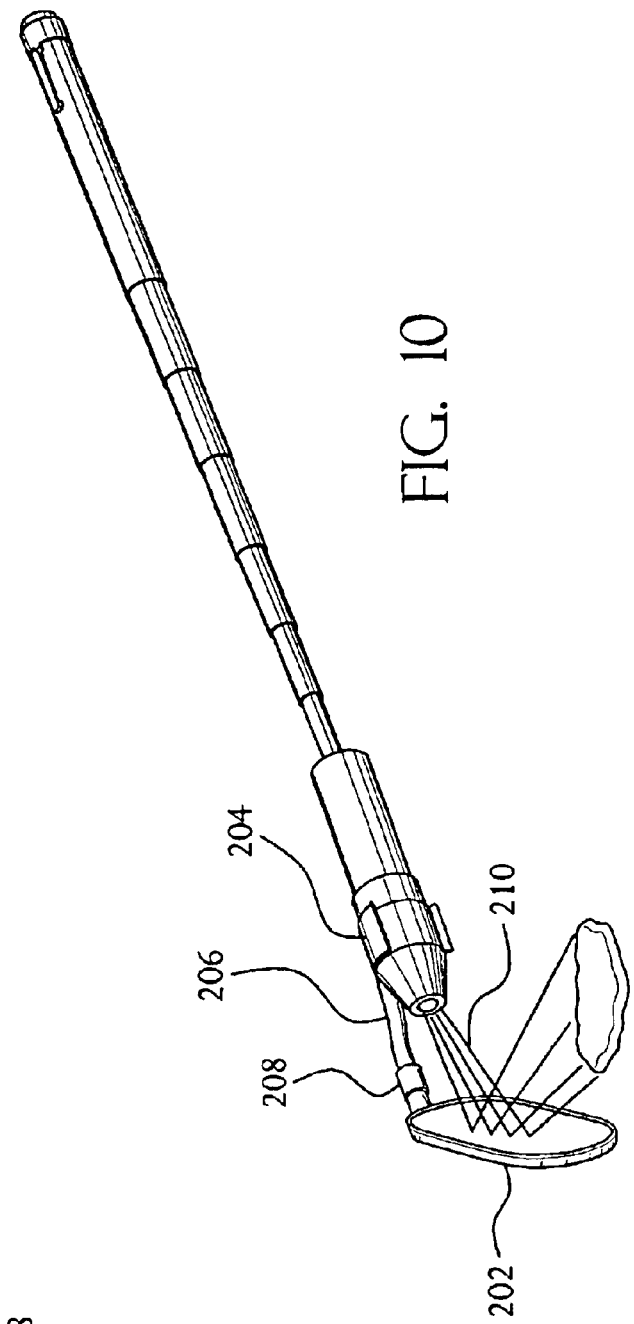

PEN SIZE LED INSPECTION LAMP FOR DETECTING FLUORESCENT MATERIAL

CROSS-REFERENCE TO RELATED APPLICATION

This application is a continuation-in-part of U.S. application Ser. No. 09/899,796, filed Jul. 5, 2001 now U.S. Pat. No. 6,491,408.

FIELD OF THE INVENTION

The invention relates to the general field of inspection lamps utilized for detection of fluorescent materials.

BACKGROUND OF THE INVENTION

Leak detection and surface flaw non-destructive testing techniques often use fluorescent dye additives or fluorescent penetrants. These techniques rely upon the unique physical property of various materials to fluoresce when excited by certain wavelengths of light.

Fluorescence is generally understood to be a property that enables some materials to absorb light energy and to radiate visible light at a longer wavelength than the absorbed light. According to generally accepted theory, electrons in fluorescent materials are excited upon being illuminated by light energy of a specific absorption band wavelength, and emit light energy in a longer wavelength response band as the electrons return to the unexcited or ground state. The specific excitation and response wavelengths are characteristics of the particular fluorescent materials.

The apparent brightness of a fluorescent material's luminescence is dependent on the wavelength and the intensity of the incident radiation. The excitation band generally has one or more peak wavelengths that will produce a greater response than incident light of the same intensity at an off-peak wavelength. Thus, a fluorescent material which has an excitation peak at a specific wavelength may exhibit a much reduced luminescence as the wavelength of incident light deviates from the excitation peak, and will lose the ability to fluoresce when the incident light does not provide enough energy within the excitation range.

For example, two commonly used fluorescent leak detection dyes are perylene-based fluorescent compounds and naphthalimide-based fluorescent compounds. Perylene dyes produce a yellow fluorescent response when exposed to incident radiation which includes the UV-A wavelength band of about 315 nm to about 400 nm, with a strong peak between about 340 to 375 nm. Naphthalimide dyes fluoresce green when exposed to incident radiation of visible violet/blue light in a range from about 400 nm to about 480 nm.

A fluorescent response is more visible when the intensity of other visible light is reduced, so that the fluorescent response is not masked or washed-out by other light. The various UV-A or Violet/Blue inspection lamps use several types of light sources and filtering to produce a light output in the excitation bands with little or no output light in the fluorescent response band. For example, a lamp having a high intensity incandescent light source with a narrow band UV (360–370 nm) absorption filter will emit light energy concentrated around the excitation peak of a perylene dye additive. An inspection lamp with a wider band UV/BLUE absorption filter centered at about 400 nm provides output in the UVA and visible violet/blue range, with the greatest intensity centered in the excitation band of a common naphthalimide dye compound. In the absorption filter lamps, however, the larger portion of light energy in the visible and infrared wavelengths is absorbed as heat in the filter.

A more efficient inspection lamp uses thin-film dichroic reflectance filter. A dichroic filter can be tailored to reflect back into the lamp only the range of visible wavelengths outside of the chosen excitation band, while passing the other wavelengths. Because the emitted light is not converted to heat in the dichroic filter, the lamp can be made considerably more compact than the lamps with absorption filters.

All of the above-described prior lamps use a broad spectrum light source, and thus require some type of filtering, whether absorption or dichroic, to transmit light in an excitation band while restricting light output in the visible fluorescent response band. In the present invention, however, the inspection lamp uses the narrow band electroluminescence of solid state lamps, specifically light-emitting diodes (hereinafter referred to as "LEDs") with glass envelopes that refract light to the tip of the envelope. LEDs have been known for many years, but until recent developments it has been difficult to obtain sufficiently high levels of luminous flux as would be required for an inspection lamp. This problem was particularly acute for LEDs emitting in the blue to UV bands, which produced much less lumens per watt than the red, yellow and green emitting LEDs. [See, Lighting Handbook, $8^{th}$ edition, Illuminating Engineers Society of North America, Chapter 6, figure 6.68(f)].

Recent developments in nitride semiconductor materials, particularly gallium nitride (GaN) based epitaxal structures, have provided more efficient LEDs that can produce sufficient lumens for an inspection lamp in the UV 360–390 nm range. For example, a GaN electroluminescent device as described in U.S. Pat. No. 5,898,185 has an emission peak at 380 nm. An LED emitting in the 360 nm–390 nm range would make a useful light source for detection of a perylene dye.

GaN alloys can produce other useful emission bands. The same patent describes a commercial GaInAlN LED that emits blue light at 460 nm. The light emission wavelengths of GaN LEDs can also be altered by phosphor films if desired. As described in the specification of the U.S. Pat. No. 5,898,185, these GaN-based LEDs have high efficiencies, typically in the energy emitted/power-in range of 10%.

The invention uses these LED light sources in the form of a LED bulb in which the glass lens capsule directs light to the rounded tip of the capsule. This causes a narrow high intensity focus at the tip and a diverging beam emanating from the tip. The effect is having a highest light intensity at the capsule tip and a rapidly decreasing intensity as distance from the tip increases. Thus, while the intensity at close distances may be sufficient to excite a strong response from a fluorescent dye, the intensity at longer distances may not be enough to produce the fluorescent response.

An LED inspection lamp can be very small, in fact, it can be the size of a pen light powered by AAAA sized batteries. A current LED pen light, the STYLUS™ model with an "Ice Blue" emitting LED is only 0.38 inches in diameter and 6.60 inches in length and operates on three AAAA batteries with a run time of over 10 hours, yet it has sufficient blue light output to cause a fluorescent response in a naphthalimide-based leak detection additive from a distance of 18 inches in dark conditions. Even in daylight conditions, it can excite a naphthalimide dye to a bright response at one to six inches.

Although the narrow shape of the LED pen light is helpful in allowing the LED capsule to be inserted into narrow areas close to a suspected leak site, it is still restricted by its length. Furthermore, the metal handle and battery housing is inflexible. Both the short length and inflexibility can make it difficult or impossible to reach areas of potential leak sites, such as lines and connectors in the circuit of an automobile air conditioner.

It would therefore be useful to provide an LED lamp that has a high intensity focus at the tip as well as an extendible handle so that the lamp may be inserted deeply into tight areas to bring the tip of the LED capsule close to the potential leak site to be investigated for fluorescent material. An extendible handle may alternatively be flexible to aid in insertion around obstructions. An alternative embodiment lamp may have two or more different color LEDs, such as violet and blue, which may be selectively used to detect more than one type of fluorescent material, or may have an LED and a white light bulb to select between general illumination and fluorescent detection. An LED lamp with an extendible handle may also have a mirror attached to permit inspect under or around an obstruction.

SUMMARY OF THE INVENTION

In accordance with the present invention, there is provided an inspection lamp for detecting fluorescent materials. The inspection lamp includes a housing, an extendible handle, and at least one LED, and may include a mirror.

BRIEF DESCRIPTION OF THE DRAWINGS

For the purpose of illustrating the invention, there is shown in the drawings a form which is currently preferred; it being understood, however, that this invention is not limited to the precise arrangements and instrumentalities shown.

FIG. 9 is an isometric view of an embodiment of the inspection lamp that includes an attached mirror.

FIG. 10 is an isometric view of the embodiment in FIG. 9 showing a telescoping handle and the light emitted from the LED reflected in the mirror.

DESCRIPTION OF THE INVENTION

Figure 1:
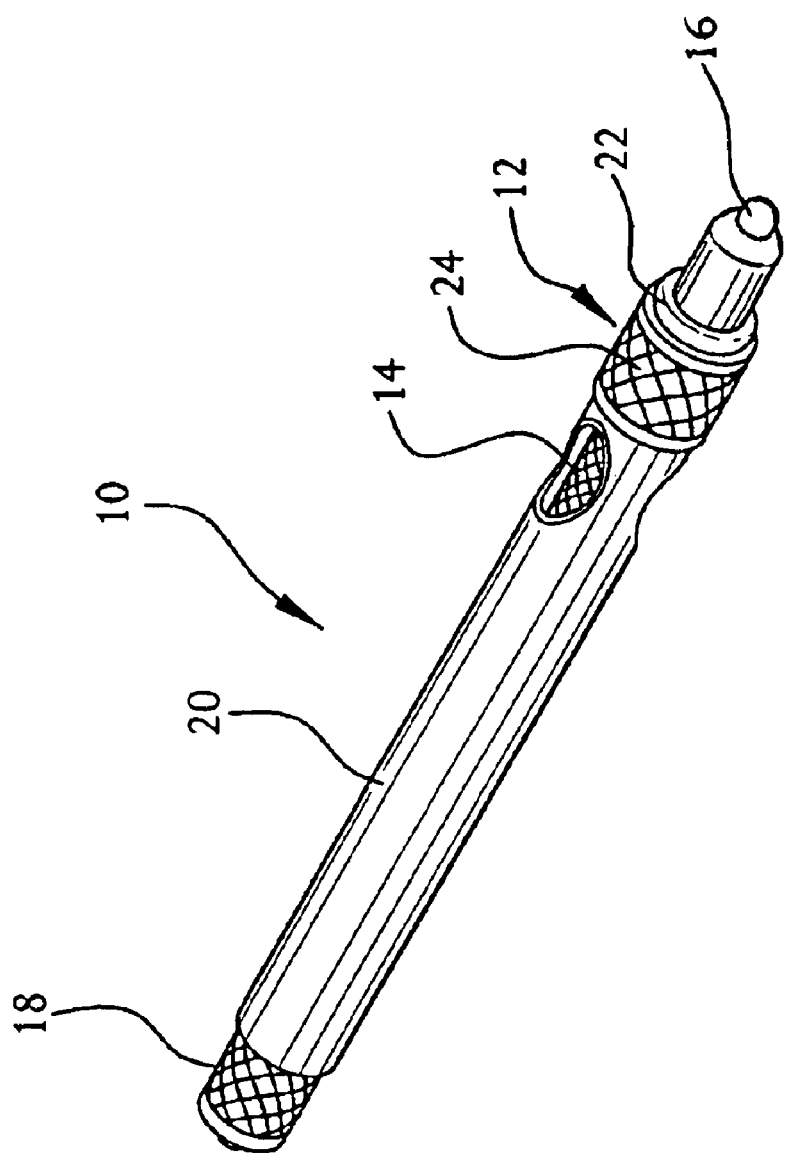
FIG. 1 is an isometric view of an embodiment of the inspection lamp in accordance with the present invention.
Figure 2:
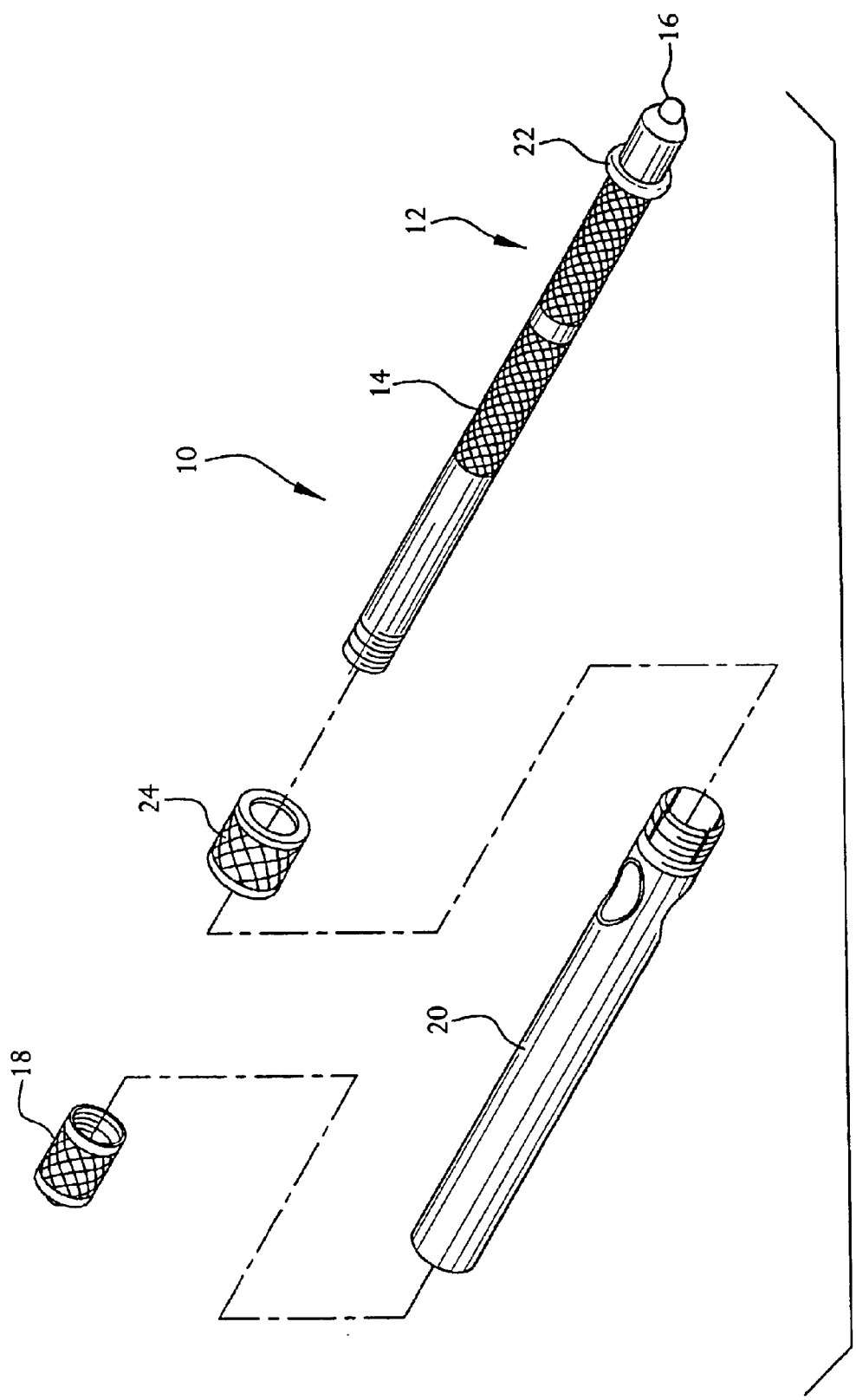
FIG. 2 is an exploded isometric view of an embodiment of the inspection lamp in accordance with the present invention.

FIGS. 1–4 show an embodiment of an inspection lamp 10 in accordance with the invention. This embodiment of inspection lamp 10 includes an LED pen light 12 having an aluminum housing 14. In this embodiment, shown in FIG. 2, a rear end of the housing is threaded while the front end includes an aperture for receiving a glass lens capsule 16. The housing 14 is adapted to enclose the LED pen light's batteries, switch contacts and light source. The pen light 12 uses a blue LED as its light source. The glass lens capsule 16 of the LED extends out through the front end of the housing. An example of a suitable commercially available LED pen light of this type is the STYLUS3 "ICE BLUE" penlight by Streamlight®.

The bottom of the pen light housing 14 has a screw cap 18 that also serves as an ON/OFF switch by pressing the batteries into an electrical connection, either by tightening the screw cap or by pressing a momentary switch at the back of the cap.

A hollow extendible handle 20 is adapted to slidingly engage around the housing 14 of the LED pen light. The top end of the extendible handle is adapted to receive a locking mechanism 24 for locking the handle in a desired position relative to the housing, in effect extending the handle of the inspection lamp 10 to a desired length. In this embodiment, the top end of the handle is threaded and slotted, while the locking mechanism is a threaded collar. When the collar 24 is tightened to the bottom of the threads, it compresses the slotted tip of the handle and presses it against the pen light housing to keep the pen light from sliding within the handle. A stop ring 22 is provided around the pen light housing to prevent the collar from slipping off the front end of the pen light.

Figure 3:
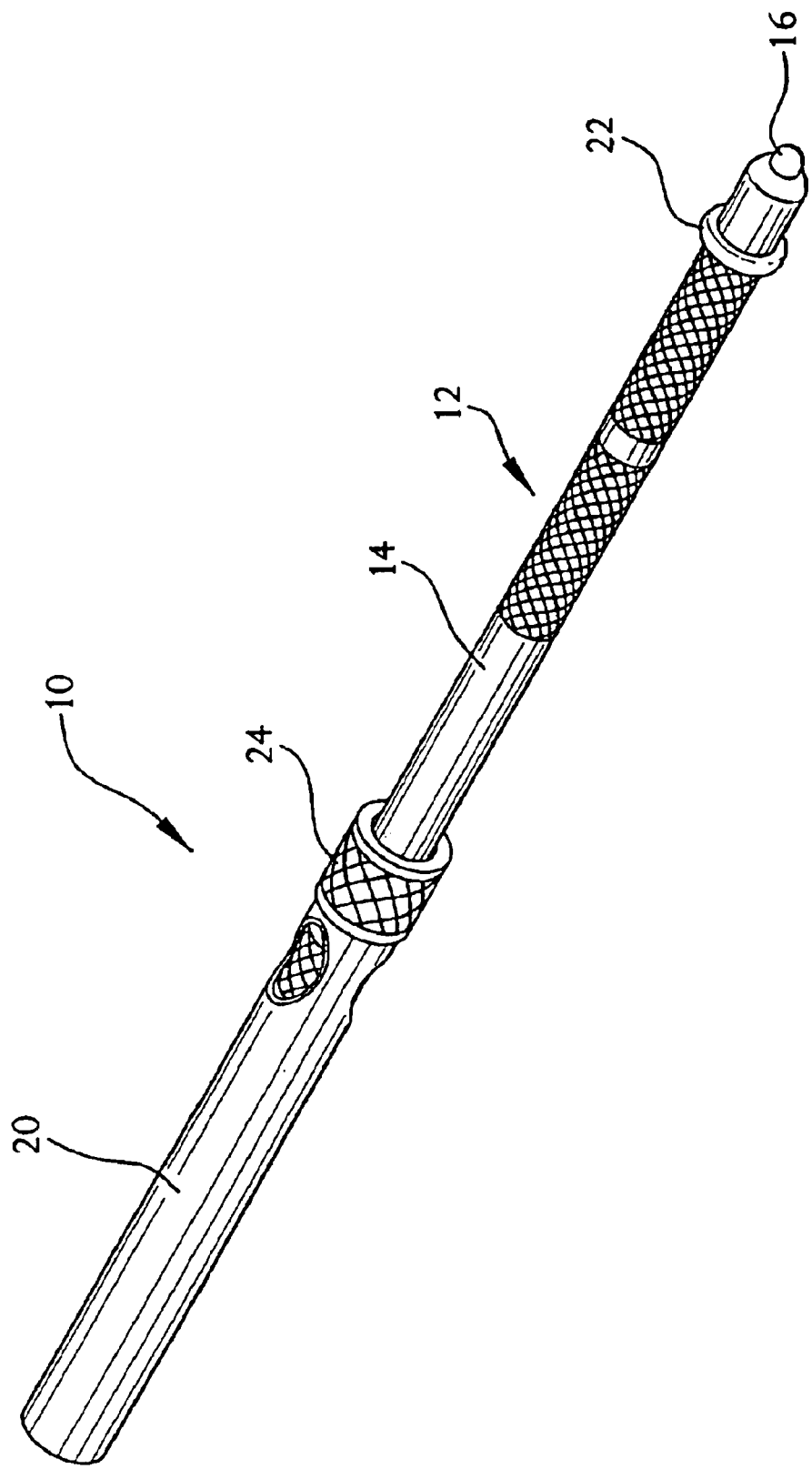
FIG. 3 is an isometric view of an embodiment of the inspection lamp in accordance with the present invention.
Figure 4:
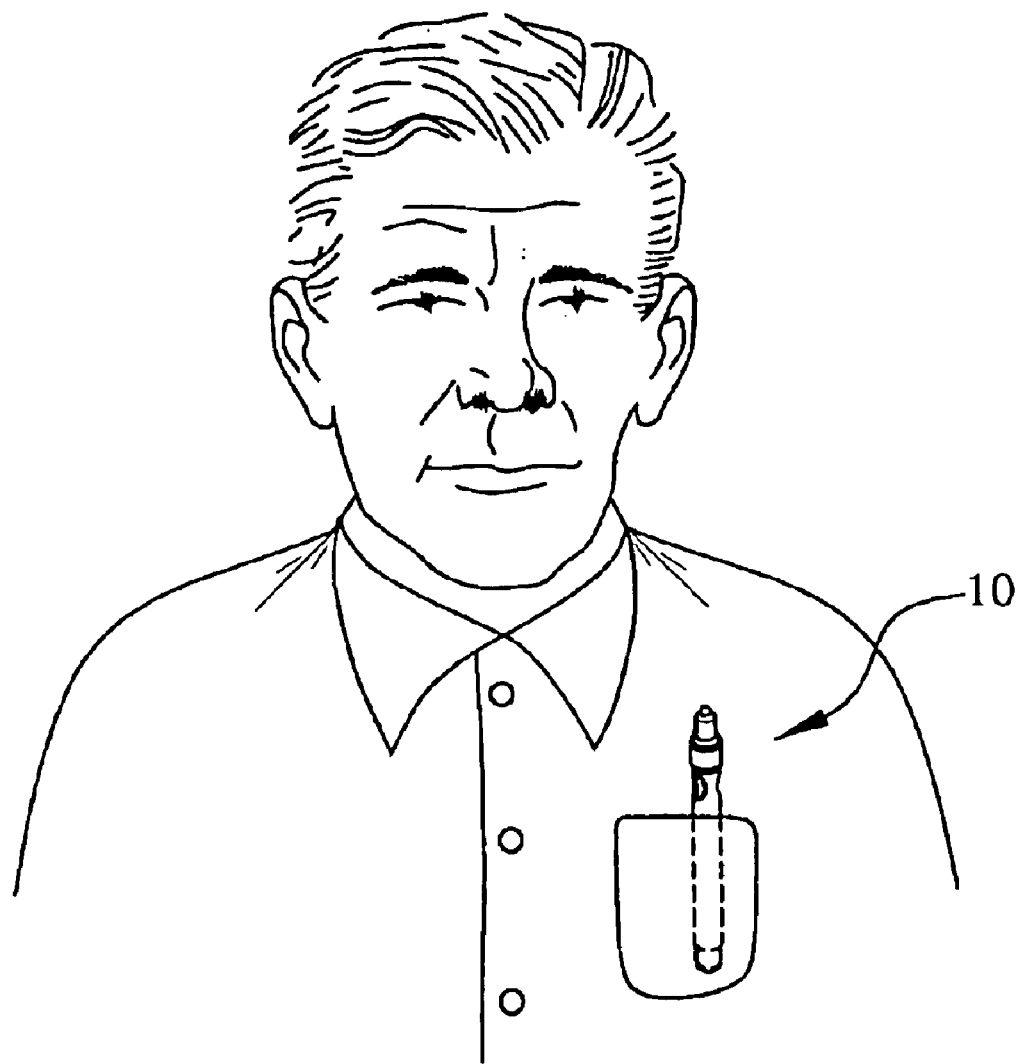
FIG. 4 is an illustration of a human being with an embodiment of the inspection lamp in his shirt pocket.

In FIG. 1, the inspection lamp is shown locked in a fully retracted position. FIG. 3 shows the same lamp locked in a fully extended position. FIG. 4 shows the inspection lamp carried as a pen light inside a shirt pocket so as to illustrate the lamp's relative size.

The light from the LED is directed through the rounded tip of the glass lens capsule. Thus, the emitted light beam has its highest light intensity in a narrow beam at the tip of the glass capsule 16, and the beam diverges as distance from the tip increases.

Figure 5A:
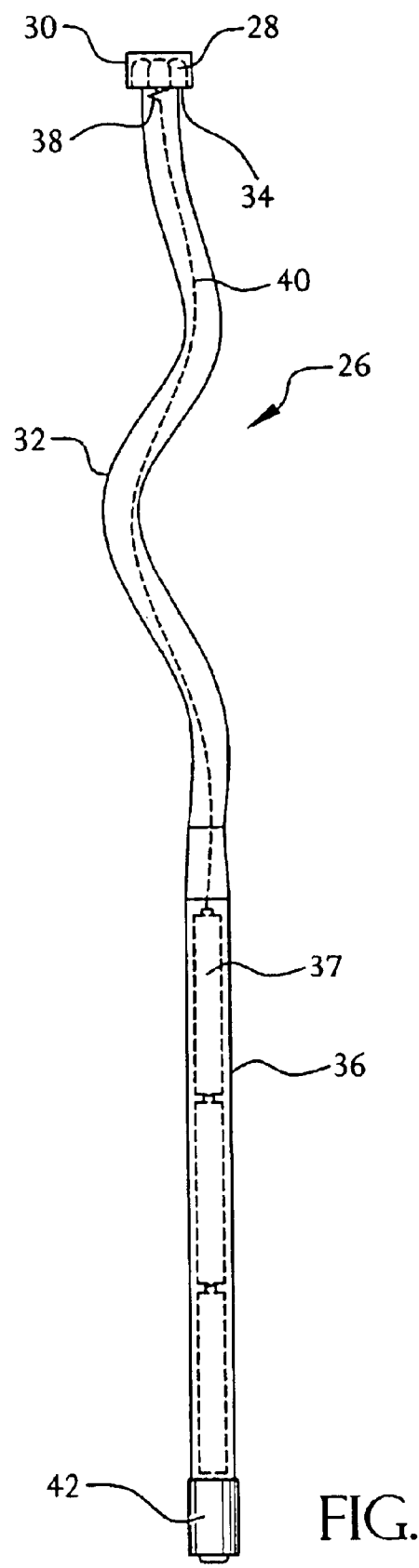
FIG. 5A is a side elevation view of an embodiment of the inspection lamp in accordance with the present invention.
Figure 5B:
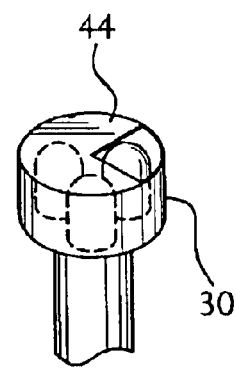
FIG. 5B is an isometric view of the lamp housing of an embodiment of the inspection lamp in accordance with the present invention.

In FIGS. 5A and 5B, an alternative embodiment inspection lamp 26 uses three LEDs 28 inside a lamp housing 30. The lamp housing 30 is attached to an extendible handle 26 having an upper flexible portion 32 and a lower rigid portion 36 of the inspection lamp. The upper flexible portion 32 includes a hollow cavity and can be adjusted and extended as desired. The upper flexible portion 32 can be folded onto the lower rigid portion 36 to shorten the length of the inspection lamp.

The underside of the lamp housing 34 includes electrical contacts 38 to connect the LEDs 28 to a conductor wire 40. The wire 40 extends downward from the electrical contact 38 through the upper flexible portion 32 to connect with the batteries 37. The lower rigid portion 36 includes a removable cap 42. The removable cap 42 includes a metallic coil for completing the circuit in the typical fashion to power the LEDs 28.

FIG. 5B shows a closer view of the lamp housing 30. The top side of the lamp housing includes a rotatable cover 44 with an aperture suitable for only one LED for selectively blocking the light from two of the LEDs, so that only the light from one LED is emitted from the inspection lamp at any one time. The lamp housing 30 may contain different LEDs 28 and may also include an incandescent lamp or other suitable source of white light.

For example, the lamp may contain three LEDs, one in each of ultraviolet, blue, and green. Depending on the fluorescent dye being used, the cover can be rotated so that only the appropriate LED is emitted by the inspection lamp. For instance, if a perylene-based fluorescent compound is being used, the ultraviolet LED may be selected. When using a naphthalimide-based fluorescent compound, the blue LED may be selected.

Figures 6A, 6B:
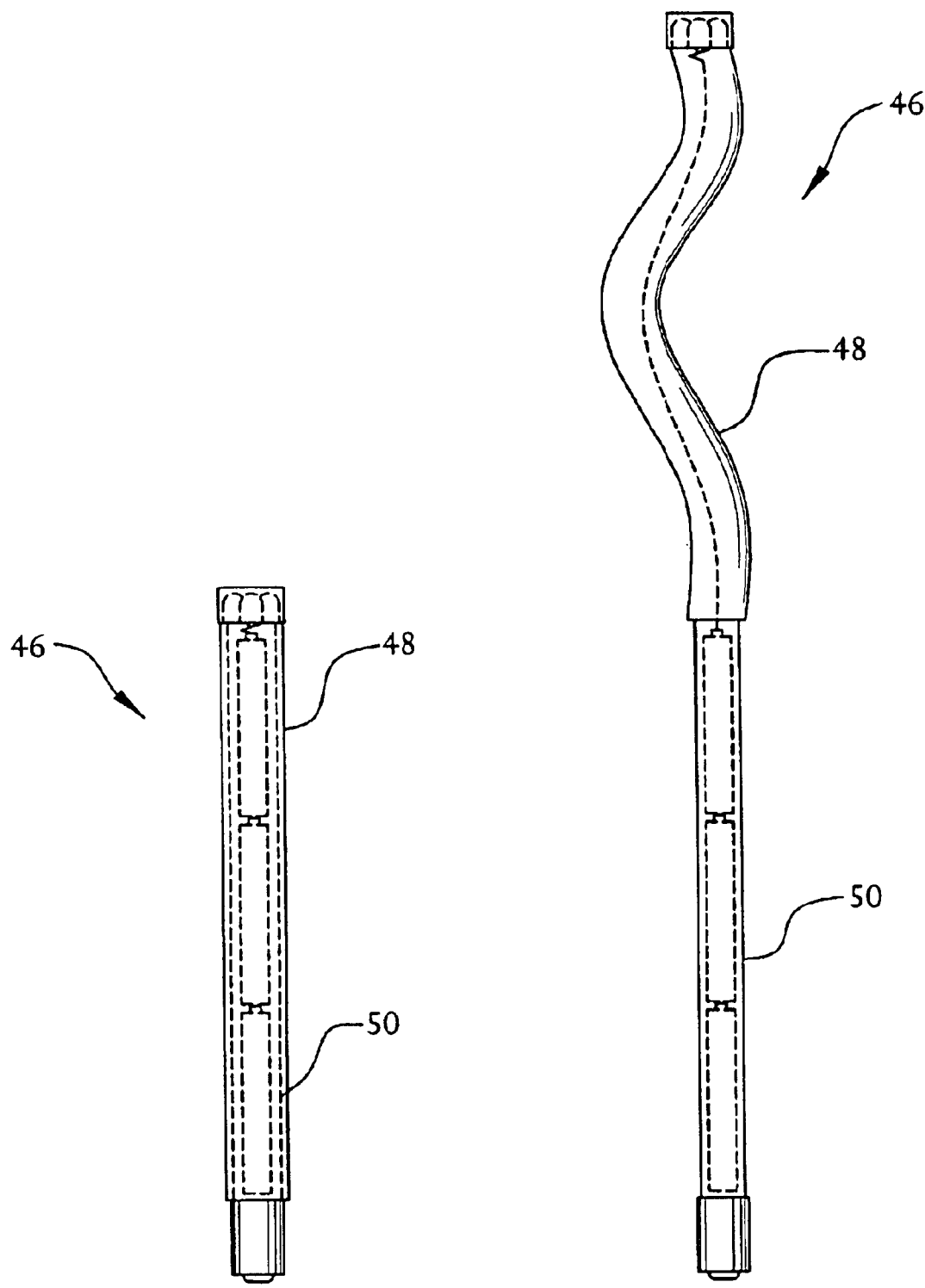
FIG. 6A is a side elevation view of an embodiment of the inspection lamp in which the lamp is in the unextended position in accordance with the present invention.
FIG. 6B is a side elevation view of an embodiment of the inspection lamp in which the lamp is extended in accordance with the present invention.

Shown in FIGS. 6A and 6B is another embodiment where the pen-size inspection lamp has an extendible handle 46 which is at least part flexible. An upper flexible portion 48 is slidably engaged with the lower rigid portion 50. The upper flexible portion 48 has an inner diameter greater than the outer diameter of the lower rigid portion 50. FIG. 6A shows the inspection lamp in a non-flexed and non-extended position. FIG. 6B shows the inspection lamp fully extended and partially flexed.

Figures 7A, 7B:
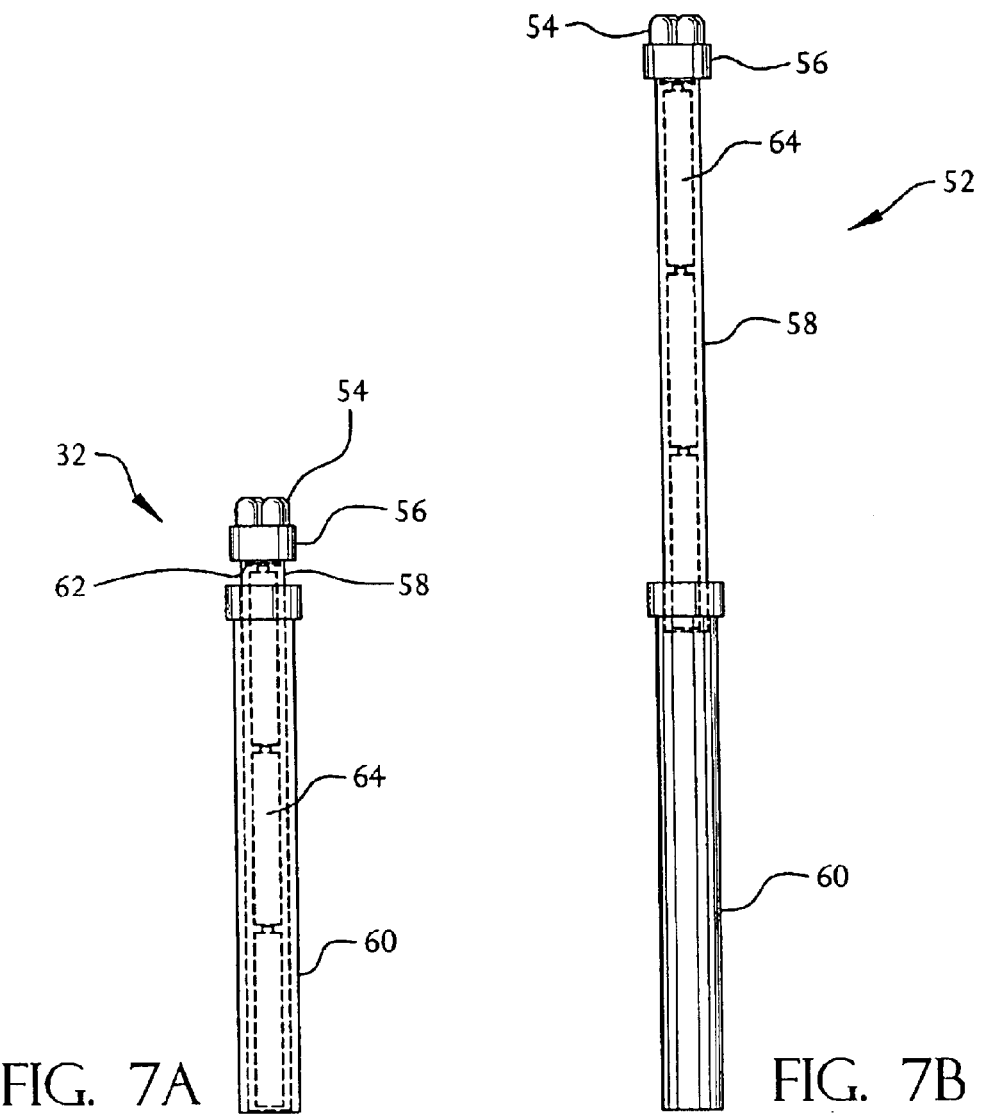
FIG. 7A is a side elevation view of an embodiment of the inspection lamp in which the lamp is in the unextended position in accordance with the present invention.
FIG. 7B is a side elevation view of an embodiment of the inspection lamp in which the lamp is extended in accordance with the present invention.
Figure 7C:
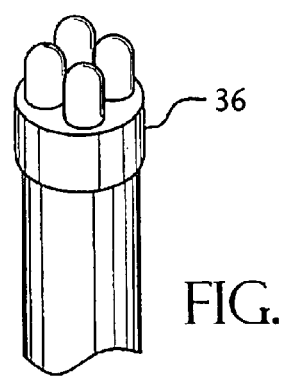
FIG. 7C is an isometric view of the lamp housing of an embodiment of the inspection lamp in accordance with the present invention.

FIGS. 7A, 7B, and 7C show another embodiment of the present invention, in which the inspection lamp has four LEDs 54 attached to a lamp housing 56. An incandescent lamp or other source of white light may substituted for one of the LEDs. The lamp housing is rotatably attached to an upper portion 58 of an extendible handle 52. The extendible handle 52 comprises the upper portion 58 and a lower portion 60. The upper portion 58 is slidably engaged with the lower portion 60. The outer diameter of the upper portion 58 is less than the inner diameter of the lower portion 60. The upper portion 58 and lower portion 60 include a hollow cavity as shown in FIGS. 7A and 7B. In a preferred embodiment, the hollow cavity of the upper portion 58 contains a power source. In the same embodiment, the power source is an internal power source comprising at least one battery 64.

The underside of the lamp housing 56 includes a plurality of electrical contacts 62. The number of electrical contacts 62 located at the underside of the lamp housing 56 corresponds to the number of LEDs and sources of white light 54 attached to the lamp housing 56. As noted earlier, when working with leak detection dyes, certain LEDs work most efficiently in conjunction with certain fluorescent compounds. In one embodiment, three LEDs, ultraviolet, blue, and green, and one source of white light are attached to the lamp housing. In order to selectively illuminate a single LED or source of white light, the lamp housing 56 is rotated so as to cause the electrical contact of the desired LED or white light to contact the inspection lamp's source of power. For instance, if the green LED is to be emitted by the inspection lamp, the lamp housing 56 is rotated so as to cause the green LED's electrical contact to connect with the power source.

The embodiment of the present invention shown in FIGS. 7A and 7B may be extended to illuminate hard-to-reach areas. FIG. 7B shows the inspection lamp fully extended.

Figure 8:
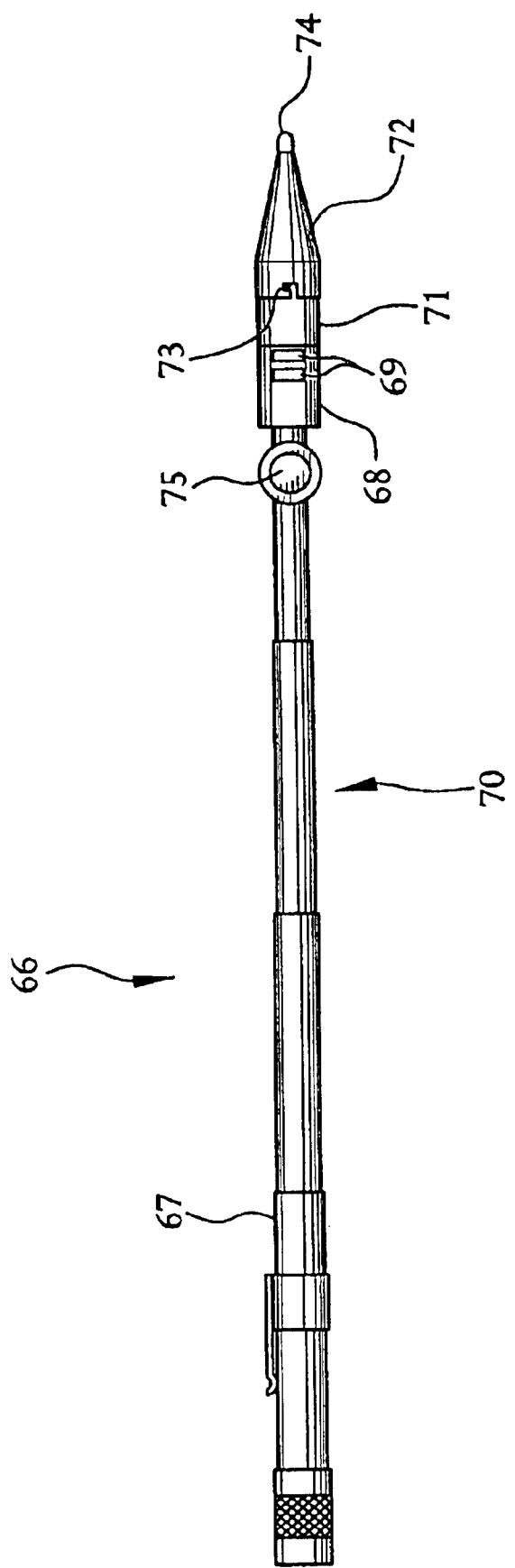
FIG. 8 is an isometric view of an embodiment of the inspection lamp in which the inspection lamp includes a telescoping handle.

Referring now to FIG. 8, another embodiment of the present invention is shown in which the inspection lamp 66 includes an extendible handle 67 and a removable LED lamp assembly 72. In this embodiment, the extendible handle 67 is comprised of a plurality of slidingly engaged cylinders 70 of sequentially reduced diameter to facilitate the handle's ability to extend and contract in a telescoping manner. The telescoping handle 67 may be comprised of any number of cylinders and those cylinders may be of any size or shape. For instance, the circular section cylinders may be replaced with hollow square cylinders. In FIG. 8, the handle is shown in an extended position.

In one embodiment of the inspection lamp 66 shown in FIG. 8, there is a battery housing 68 opposite the telescoping handle 67. The battery housing 68 may include controls 69 for connecting the LED lamp assembly 72 to at least one battery and to have a threaded top (not shown) for releasably engaging a screw cap 71. The battery housing 68 is configured to accept coin-sized batteries (not shown) to provide electrical power to the LED lamp assembly 72. The LED lamp assembly 72 is releasably attached to the screw cap 71. In the depicted embodiment, the LED lamp assembly 72 may be locked in place with a locking mechanism, an example of which is shown in FIG. 8, numeral 73. The locking device 73 shown in FIG. 8 is simply shown as an example; those skilled in the art will realize that many arrangements capable of releasably locking the LED lamp assembly 72 to the screw cap 71 could be used.

In a preferred embodiment, the LED lamp assembly 72 includes an LED 74 with a wavelength band having a peak intensity below about 500 nm. It is important to note however, that the LED lamp assemblies 72 are interchangeable, and thus the lamp 66 may be configured with an LED having any wavelength band. Therefore, if it is desirable to utilize an LED of a particular color, the user may simply replace the LED lamp assembly 72 with an LED lamp assembly 72 having the color of choice. For instance, a user using the inspection lamp 66 with a LED lamp assembly 72 having a blue LED may find it desirable to use a LED lamp assembly 72 having a green LED. If so, the user may simply remove the LED lamp assembly 72 having a blue LED and replace it with a LED lamp assembly 72 having a green LED.

In other embodiments, where the LED lamp assembly 72 may include two or more LEDs, it is preferable if at least one LED has a wavelength band with a peak intensity below about 500 nm. In such an embodiment, the controls 69 are adapted to selectively illuminate at least one LED, as desired.

In a preferred embodiment, there is a hinge 75 located between the handle 70 and the housing 68, as shown in FIG. 8. In other embodiments, where a hinge is not present, housing 68 is simply attached to the telescoping handle 70.

It is important to note that the various forms of extendible handles as well as the manner in which the various embodiments are able to emit a single LED or white light and are able to extend and flex is completely interchangeable. For example, the lamp housing 30 and cover 44 used for selectively emitting a single LED as shown in FIGS. 5A and 5B may be utilized with the upper 58 and lower 60 cylindrical portions shown in FIGS. 7A and 7B.

In other embodiments, aspects of the handle may include alternative means for extending the inspection lamp from a shorter configuration to a longer configuration. Such means may include, for example, a spring and release mechanism for causing the inspection lamp to quickly extend by activating the release of a spring-type mechanism or other device capable of causing the inspection lamp to quickly extend. A means for extending the inspection lamp may also be configured similar in operation to a typical jack knife that is folded in half and locked when not in use. Such a configuration could include a hinge, ball-joint or other suitable element for causing the lamp to be collapsed approximately in half. A configuration could also include a locking mechanism so that the lamp is locked into place when collapsed or folded, as well as a release mechanism for releasing the lock. The release could be employed with or without a spring-type mechanism.

FIGS. 9 and 10 show an embodiment of the invention in which a mirror assembly 200 is attached to the pen size LED lamp of FIG. 8. The mirror assembly comprises a mirror 202, a clip 204 for attaching the mirror to the LED lamp assembly, an arm 206 extending from the clip to the mirror, and a hinge 208 which allows the mirror to be rotated to different reflection angles with respect to the LED assembly. The mirror assembly is clipped onto the LED assembly 172 at or near the battery housing 168. The clip allows the mirror assembly to be removed from the lamp, and to be attached to the lamp with the arm lying along the lamp for storage or extending in front of the lamp for use in leak detection.

A similar mirror assembly may be attached to others of the various embodiments of the LED lamp. For example, in the embodiment shown in FIGS. 1 to 4, the mirror assembly may be clipped at or near stop ring 22. For the embodiment shown in FIGS. 5 and 6, the mirror assembly may be attached to the flexible portion 32, 48 of extendible handle 26, 52 at or near the LED lamp housing 30. For the embodiment shown in FIG. 7, the mirror assembly may be attached at or near handle 64 after extension and close to lamp housing 56.

Adding the mirror assembly to the lamp increases the ability to detect fluorescent material in hard-to-see areas such as around corners or underside surfaces. As shown in FIG. 10, the user may rotate the mirror so that it reflects the emitted light 210 from the LEDs at an angle set by rotating the mirror on the hinge. The user may then position the mirror to reflect onto a location that cannot be illuminated directly by the LED so that the location may be viewed in the mirror. If fluorescent leak detection material is present, illumination by the LED light reflected off the mirror will produce a fluorescent response and indicate a leak at the location. The mirror will be particularly useful in detecting leaks that occur on the underside or out-of-view portion of air conditioner components, hoses or fittings that cannot be easily accessed for direct observation.

The invention may also be embodied in other specific forms without departing from the spirit or essential attributes thereof and, accordingly, reference should be made to the appended claims, rather than to the foregoing specification, as indicating the scope of the invention.

What is claimed is:

1. An inspection lamp for detecting refrigerant leaks from air-conditioning systems through illumination of fluorescent material added to the refrigerant, the inspection lamp comprising an LED pen light having an extendible handle and an LED lamp housing at one end of the handle, the lamp housing containing an LED, said inspection lamp further comprising;
   a mirror assembly comprising
      a mirror;
      a clip for attaching the mirror to the lamp at or near the LED lamp housing; and
      an arm extending between the clip and the mirror, said arm having a hinge connection with the mirror for rotating the mirror to different reflection angles with respect to the LED wherein the LED emits light within a wavelength band below about 500 nm.

2. An inspection lamp as in claim 1, wherein
   the handle has an upper flexible portion attached to the lamp housing and a lower portion, wherein the flexible portion may be bent to fit into hard-to-reach areas of air-conditioning systems.

3. An inspection lamp as in claim 2, wherein the LED emits light within a wavelength band below about 500 nm.

4. An inspection lamp as in claim 1, further comprising:
   the handle having a grip section and telescoping sections adapted to be pulled out to extend the handle and pushed in to retract the handle; and
   a battery housing containing a battery, the battery housing being attached at one end thereof to the telescoping section that is furthest from the grip section when the handle is extended.

5. An LED inspection lamp for detecting refrigerant leaks from air-conditioning systems through illumination of fluorescent materials added to the refrigerant and lubricating oil, said inspection lamp comprising:
   an extendable and retractable handle having a grip section and telescoping sections adapted to be pulled our to extend the handle and pushed in to retract the handle,
   a battery housing containing a battery, the battery housing being attached at one end thereof to the telescoping section that is furthest from the grip section when the handle is extended;
   an LED lamp assembly connected to the battery housing and containing an LED that emits light within a wavelength band below about 500 nm; and
   a mirror assembly having
      a mirror,
      a clip for attaching the mirror to the battery housing, and
      an arm extending between the clip and the mirror, said arm having a hinge connection with the mirror for rotating the mirror to different reflection angles with respect to the LED.

6. A handheld inspection lamp for detecting refrigerant leaks from air-conditioning systems through illumination of fluorescent materials added to the refrigerant and lubricating oil, said inspection lamp comprising:
   a lamp housing;
   at least one LED mounted within the lamp housing and adapted to emit light within a wavelength band below about 500 nm which is adapted to cause the fluorescent materials added to the refrigerant to fluoresce in response to the emitted light;
   a handle having an upper flexible portion attached to the lamp housing and a lower portion, the upper flexible portion adapted to be bent to fit into hard-to-reach areas of the air-conditioning system for illuminating leaks in those hard to reach areas by locating the lamp housing in close proximity to the component being inspected; and
   an activation button located on the handle and electrically connected to the LED for permitting activation of the LED.

7. A handheld inspection lamp as in claim 6, wherein the flexible portion may be bent so as to shorten the length of the lamp.

8. A handheld inspection lamp as in claim 6, further comprising a plurality of LEDs within the lamp housing.

9. A handheld inspection lamp as in claim 8, wherein the plurality of LEDs comprise at least one LED emitting light within a wavelength band between about 315 nm to about 400 nm.

10. A handheld inspection lamp as in claim 8, wherein the plurality of LEDs comprise at least one LED emitting light within a wavelength band between about 400 nm to about 480 nm.

11. A handheld inspection lamp as in claim 6, further comprising a mirror movably attached to the handle proximate to the lamp housing.

12. A handheld inspection lamp as in claim 6, wherein the activation button is located on the lower portion of the handle.

13. An inspection lamp as in claim 1, wherein the clip is removably attachable to the side of the lamp housing.

14. An inspection lamp as in claim 13, wherein the LED lamp assembly contains a plurality of LEDs that emits light within a wavelength band below about 500 nm, and wherein the clip is removably attachable to the side of a portion of the handle near the lamp housing.

15. An inspection lamp as in claim 14, wherein the LED lamp assembly further includes at least one source of white light, and wherein the lamp includes a switch to permit activation of the white light source separately from the other LEDs.

16. An inspection lamp for detecting refrigerant leaks from air-conditioning systems through illumination of fluorescent material added to the refrigerant, the inspection lamp comprising:
   an LED pen light having an extendible handle and an LED lamp housing at one end of the handle, the lamp housing containing at least one LED which emits light within a wavelength band below about 500 nm;
   a mirror assembly including
      a mirror;
      a clip for attaching the mirror to the lamp at or near the LED lamp housing, the clip being removably attachable to the side of the lamp housing; and
      an arm extending between the clip and the mirror, said arm having a hinge connection with the mirror for rotating the mirror to different reflection angles with respect to the LED.

17. An inspection lamp as in claim 16, wherein the handle has an upper flexible portion attached to the lamp housing and a lower portion, wherein the flexible portion may be bent to fit into hard-to-reach areas of air-conditioning systems.

18. An inspection lamp as in claim 16, wherein the LED emits light within a wavelength band corresponding to ultraviolet light.

19. Art inspection lamp as in claim 16, wherein the handle includes a grip section and telescoping sections adapted to be pulled out to extend the handle and pushed in to retract the handle, and a battery housing adapted to contain a battery, the battery housing being located adjacent to the LED housing.

20. An inspection lamp as in claim 16, wherein the inspection lamp is part of a kit that includes a dye for introducing into the air conditioning system, the dye adapted to fluoresce when illuminated by light having a wavelength below about 500 nm.

21. An inspection lamp as in claim 16, wherein the LED lamp assembly contains a plurality of LEDs that emits light within a wavelength band below about 500 nm, and wherein the clip is removably attachable to the side of a portion of the handle near the lamp housing.

22. An inspection lamp as in claim 21, wherein the LED lamp assembly further includes at least one source of white light, and wherein the lamp includes a switch to permit activation of the white light source separately from the other LEDs.

23. An inspection lamp kit for detecting refrigerant leaks from air-conditioning systems through illumination of fluorescent material added to the refrigerant, the inspection lamp kit comprising:
   an inspection lamp including an LED pen light having an extendible handle and an LED lamp housing at one end of the handle, the lamp housing containing at Least one LED which emits light within a wavelength band below about 500 nm;
   a mirror assembly including a mirror, a clip for attaching the mirror to the lamp at or near the LED lamp housing, the clip being removably, attachable to the side of the lamp housing, and an arm extending between the clip and the mirror, said arm having a hinge connection with the mirror for rotating the mirror to different reflection angles with respect to the LED; and
   a dye for introducing into the air conditioning system, the dye adapted to fluoresce when illuminated by light having a wavelength below about 500 nm.

* * * * *